(12) United States Patent
Chen

(10) Patent No.: US 7,942,956 B2
(45) Date of Patent: May 17, 2011

(54) AIR PURIFIER

(76) Inventor: Ching-Ming Chen, Yung He (TW)

( * ) Notice: Subject to any disclaimer, the term of this patent is extended or adjusted under 35 U.S.C. 154(b) by 0 days.

(21) Appl. No.: 12/512,030

(22) Filed: Jul. 30, 2009

(65) Prior Publication Data

US 2011/0023720 A1    Feb. 3, 2011

(51) Int. Cl.
*B01D 46/00*    (2006.01)
(52) U.S. Cl. ............... 96/222; 96/224; 422/186.3
(58) Field of Classification Search ........... 422/1, 22, 422/24; 55/383, 385.1, 385.2, 385.3, 385.7, 55/467, 471, 473, 472; 96/222, 224
See application file for complete search history.

(56) References Cited

U.S. PATENT DOCUMENTS

| | | | | |
|---|---|---|---|---|
| 4,078,891 A | * | 3/1978 | Madjar | 422/116 |
| 5,702,507 A | * | 12/1997 | Wang | 96/55 |
| 7,093,773 B2 | * | 8/2006 | Kuiper | 239/57 |
| 7,347,888 B2 | * | 3/2008 | Hecker et al. | 96/16 |
| 7,449,245 B2 | * | 11/2008 | Akarsu et al. | 428/432 |
| 7,537,647 B2 | * | 5/2009 | Adair et al. | 96/62 |
| 2002/0094298 A1 | * | 7/2002 | Monagan | 422/5 |
| 2002/0197186 A1 | * | 12/2002 | Murray | 422/124 |
| 2003/0230477 A1 | * | 12/2003 | Fink et al. | 204/157.3 |
| 2004/0013583 A1 | * | 1/2004 | Burkhardt | 422/186.3 |
| 2004/0238344 A1 | * | 12/2004 | Benoit et al. | 204/157.3 |
| 2005/0163648 A1 | * | 7/2005 | Liang | 422/1 |
| 2007/0107597 A1 | * | 5/2007 | Cheung | 96/16 |
| 2008/0286163 A1 | * | 11/2008 | Garfield et al. | 422/120 |
| 2009/0041632 A1 | * | 2/2009 | Day et al. | 422/121 |
| 2010/0183484 A1 | * | 7/2010 | Schmidt et al. | 422/186.3 |

FOREIGN PATENT DOCUMENTS

| | | | |
|---|---|---|---|
| JP | 10128154 | * | 5/1998 |
| WO | WO 2009091367 | * | 7/2009 |

* cited by examiner

*Primary Examiner* — Duane Smith
*Assistant Examiner* — Sonji Turner
(74) *Attorney, Agent, or Firm* — Leong C. Lei

(57) ABSTRACT

An air purifier with bactericidal and odor removal effect is disclosed. The air purifier comprises a fan module; UV light source; and light catalyst, wherein the fan module withdraws external air into the purifier and the UV light source and the light catalyst are provided at the rear section of the fan module so as to receive the external air withdrawing by the fan module, and the UV light source and the light catalyst are configured to form a passage; the radiation of UV light source onto the light catalyst causes the formation of free radicals in air which decompose bacteria, micro dust and suspension within the air, to clean air odor removal and air drying.

1 Claim, 5 Drawing Sheets

AIR PURIFIER

TECHNICAL FIELD OF THE INVENTION

The present invention relates to an air purifier, and in particular, to one which has bactericidal and odour removal effect.

DESCRIPTION OF THE PRIOR ART

Generally, there are bacteria, dust and suspensions in the air. Unpurified air or dirty air affects our health to certain extent. Conventional air purifiers in the market use high voltage impact to decompose bacteria, dust and suspension in the air. These conventional air purifiers are inconvenient to use and are not able to produce clean air. Accordingly, it is an object of the present invention to provide an air purifier which has bactericidal effect and odour removal effect and can generate purified air.

SUMMARY OF THE INVENTION

It is an object of the present invention to provide an air purifier with bactericidal and odour removal effect comprising a fan module; a UV light source; and a light catalyst, wherein the fan module draws external air into the purifier and the UV light source and the light catalyst are provided behind the fan module so as to receive the external air drawn by the fan module, and the UV light source and the light catalyst are configured to form a passage; the radiation of UV light source onto the light catalyst causes the formation of free radicals in air which decompose bacteria, micro dust and suspension within the air, thereby cleaning the air.

Yet still another object of the present invention is to provide an air purifier, wherein the fan module, UV light source and light catalyst are installed within a body, and air vents are provided respectively at the front and rear sections of the body to allow air to enter or allow air to leave.

A further object of the present invention is to provide an air purifier, wherein the UV light source includes UV LED, UV tubes or other light emitting elements which generate UV light.

Yet another object of the present invention is to provide an air purifier, wherein the upper and lower edges of the rear section of the body are provided with rails for the mounting of a fragrant or essence oil allowing fragrant air to be released to the air from the rear air vent.

Other objects, and advantages will become more apparent in view of the following detailed description in conjunction with the accompanying drawings.

DETAILED DESCRIPTION OF THE PREFERRED EMBODIMENTS

Figure 1:
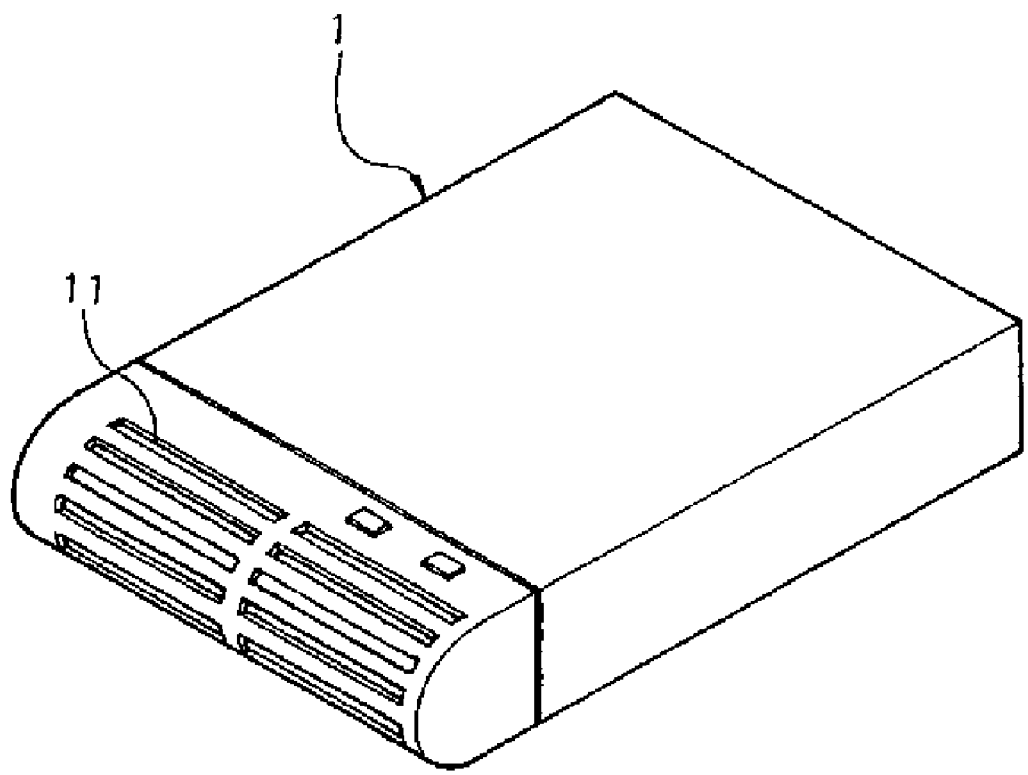
FIG. 1 shows a perspective view of an air purifier of the present invention.
Figure 2:
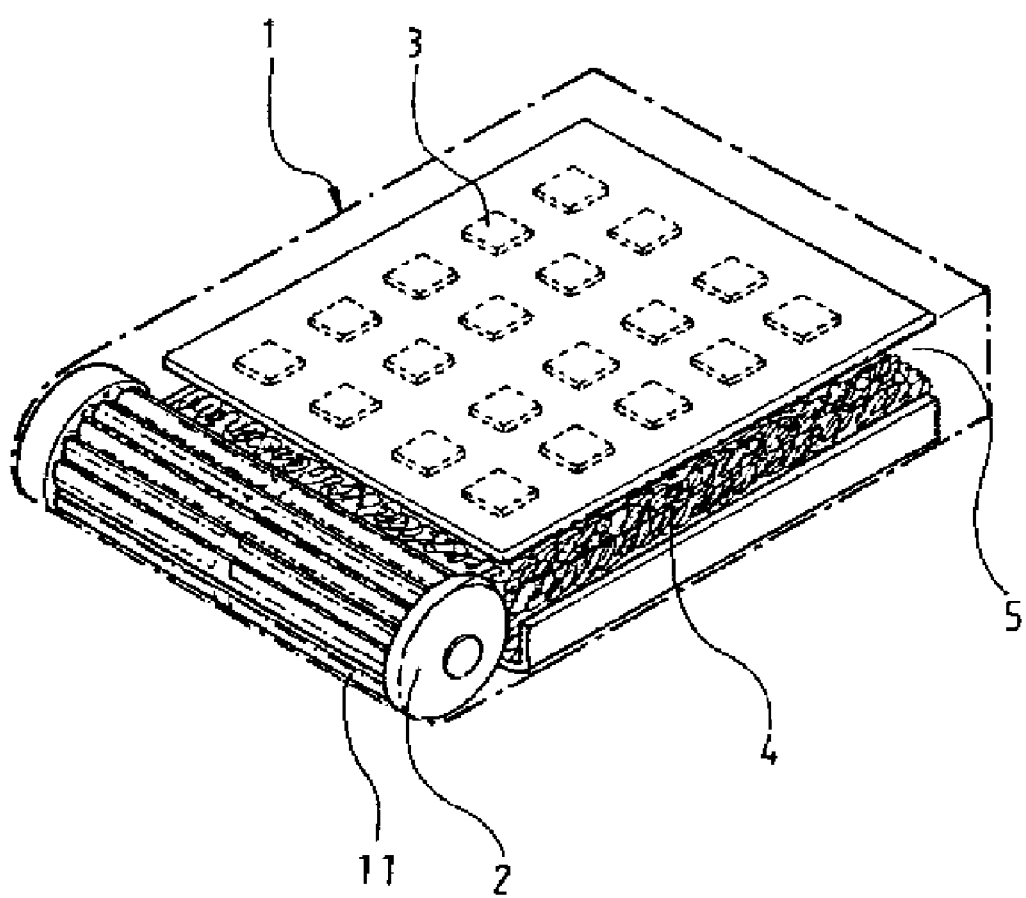
FIG. 2 schematically shows the structure of an air purifier of the present invention.
Figure 3:
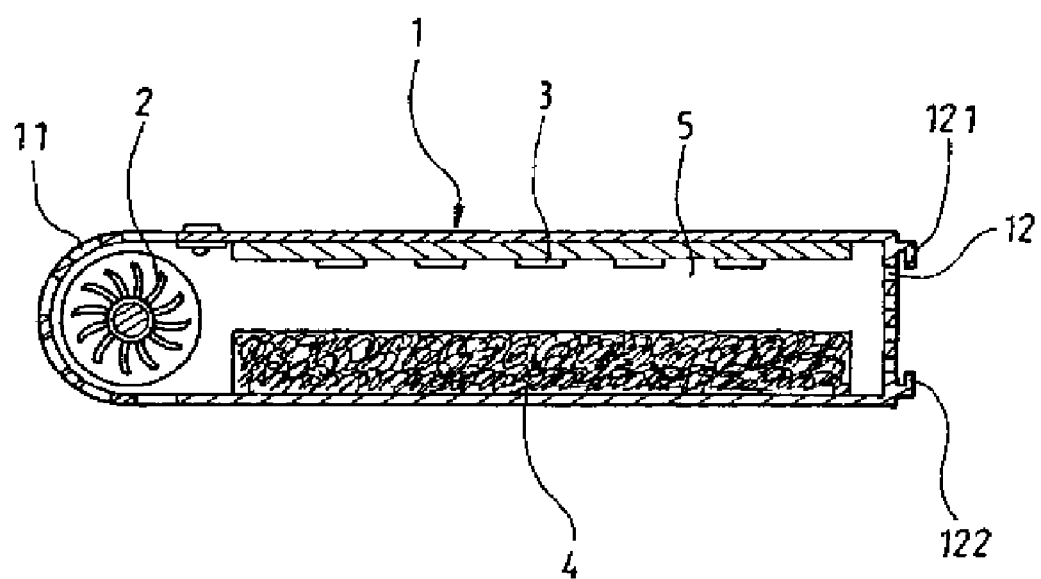
FIG. 3 shows a sectional view of an air purifier of the present invention.

Referring to FIGS. 1 to 3, there is shown an air purifier in accordance with the present invention. The air purifier comprises a body 1, a fan module 2 mounted in the body 1, a UV light source 3 and a light catalyst 4 mounted at the rear section of the fan module 2. The front and rear sections of the body 1 are provided with vents 11, 12 to allow air to enter and to leave the air purifier. The fan module 2 draws external air to the air purifier, and the UV light source 3 and the light catalyst 4 are mounted behind the fan module 2 to receive the external air drawn by the fan module 2. The upper and lower edges of the rear section of the body 1 are provided with rails 121, 122, for the mounting of fragrant or essence oil.

The UV light source 3 includes UV LED, UV tubes and other light emitting elements which generate UV light. The light catalyst 4 is provided under the UV light source 3, and the UV light source 3 and the light catalyst 4 are at a distance apart and are configured to form a passage 5 to allow external air to pass through.

The fan module 2 of the air purifier is used for drawing external air into the body 1. The UV light source 3 and the light catalyst 4 receive the external air drawn by the fan module 2 such that the external air passes through the passage 5. The UV light source 3 radiates onto the light catalyst 4 such that the air generates free radicals which decomposes bacteria, dust particles, suspensions, etc. The cleaned air is then discharged. Thus, the air purifier of the present invention provides the effect of air cleaning, odour removal and drying.

Figure 4:
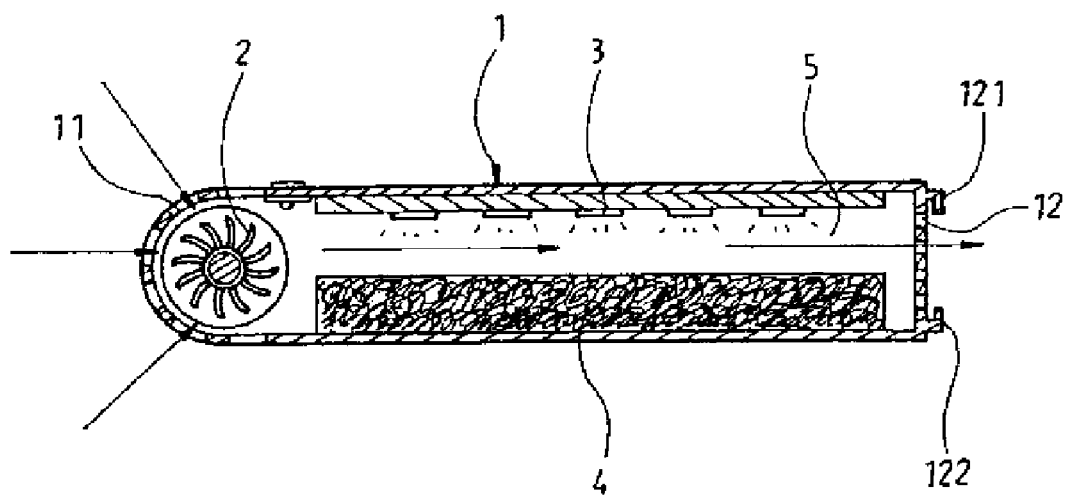
FIG. 4 shows the implementation of an air purifier of the present invention.

As shown in FIG. 4, there is shown the implementation of the air purifier of the present invention. The air purifier is placed at an appropriate location. The fan module 2 is switched on to draw air into the body 1 from the external. Air is drawn from the external into the air purifier via the air vents 11, which are located at the front section of the body 1. The UV light source 3 and the light catalyst 4 receive the external air which is drawn by the fan module 2. The external air passes through the passage 5. When the external air passes through the passage 5, the UV light source 3 radiates the light catalyst 4 such that the air generates free radicals, which decompose bacteria, dust particles, suspensions, etc in the air. The cleaned air is discharged via the vents 12 located at the rear section of the body 1. Thus the air is recycled until the air is cleaned, odour is removed and air is dried.

Figure 5:
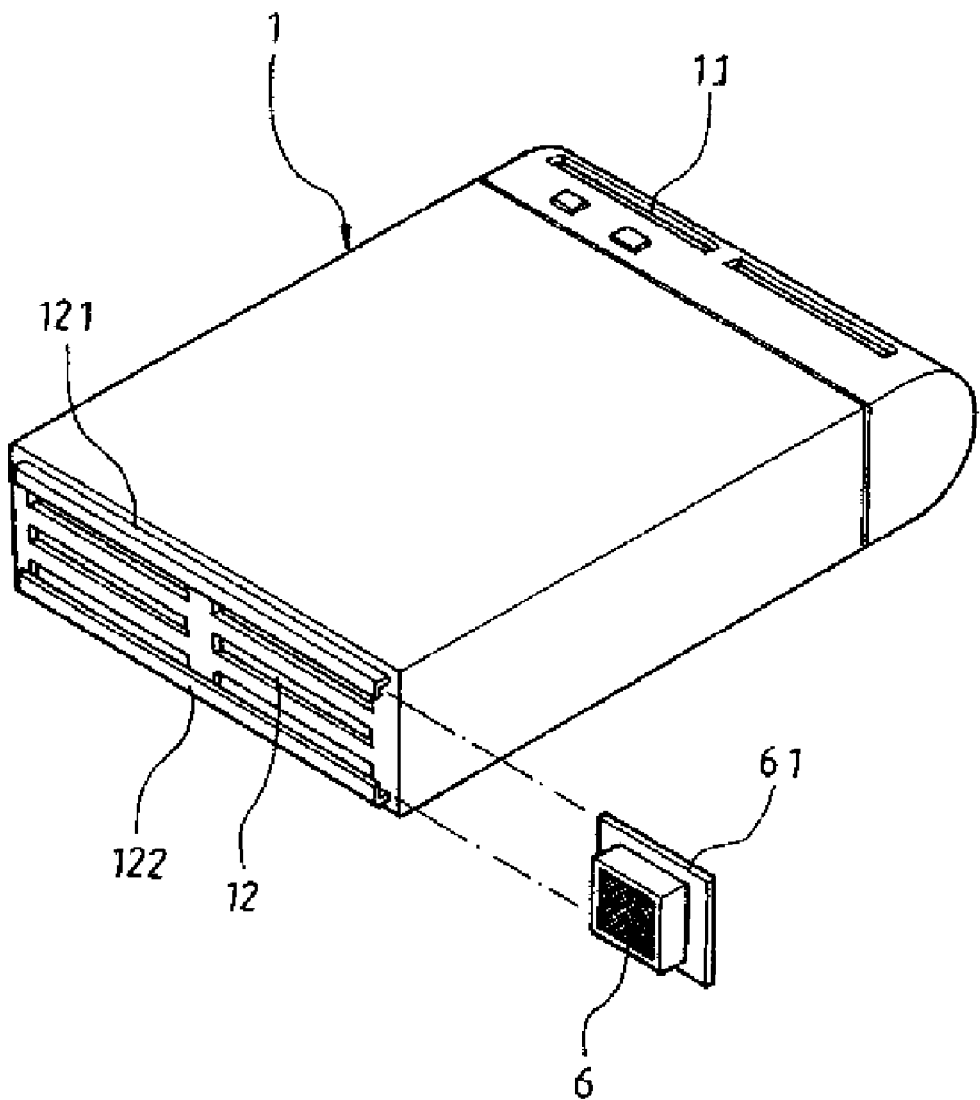
FIG. 5 shows a perspective view of the rear portion of an air purifier of the present invention.

FIG. 5 shows another implementation of the air purifier of the present invention. Referring again to FIG. 2, the upper and lower edges of the rear section of the body 1 are provided with rails 121, 122 for the mounting of fragrant 6 or essence oil. The fragrant 6 (or the essence oil) is placed into a box with a flat board 61. The flat board 61 is slid into engagement with the rails 121, 122. In application, the power switch of the UV light source 3 is switched off, and the rotating of the fan module 2 draws external air via the vents 11 positioned at the front section of the body 1. In the course of discharging the air, the fragrant 6 (or essence oil) is carried by air, and so the air has a fragrant odour.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:
1. An air purifier comprising:
   a body having a front section and a rear section each provided with a plurality of vents to allow air to enter and leave said body, said rear section having an outer side provided with an upper rail and a lower rail;

a fan module mounted at said rear section of said body for with drawing external air into said body;

a UV light source mounted on an inner top of said body;

a light catalyst mounted on an inner bottom of said body; and a container having a flat board and a box containing fragrant and mounted on said flat board, said flat board being slidably engaged with said upper and lower rails of said body;

wherein when in use, external air will be drawn into said body by said fan module and will then pass through a passage between said UV light source and said light catalyst thereby causing said external air to be purified.

* * * * *